United States Patent [19]

Quay et al.

[11] Patent Number: 5,089,644

[45] Date of Patent: Feb. 18, 1992

[54] PREPARATION OF OXAMINE COMPLEXES

[75] Inventors: Steven C. Quay, Los Altos Hills; Scott M. Rocklage, Saratoga, both of Calif.

[73] Assignee: Salutar Inc., Sunnyvale, Calif.

[21] Appl. No.: 61,933

[22] Filed: Jun. 11, 1987

Related U.S. Application Data

[63] Continuation-in-part of Ser. No. 826,827, Feb. 6, 1986, Pat. No. 4,758,422, which is a continuation-in-part of Ser. No. 688,733, Jan. 4, 1985, Pat. No. 4,637,929.

[51] Int. Cl.$^5$ ............... C07F 15/00; C07F 15/02
[52] U.S. Cl. .................. 556/40; 128/654; 128/653.2; 424/9; 436/173; 556/1; 556/45; 556/50; 556/110; 556/113; 556/116; 556/138
[58] Field of Search .............. 424/9; 514/492, 500, 514/501, 502, 836; 556/113, 146, 40-45, 50, 110, 116, 138; 600/12; 128/654; 436/173

[56] References Cited

U.S. PATENT DOCUMENTS

| | | |
|---|---|---|
| 3,118,823 | 1/1964 | Gaeumann et al. ............ 195/80 |
| 3,247,197 | 4/1966 | Gaeumann et al. ............ 260/244 |
| 3,471,476 | 10/1969 | Gaeumann et al. ............ 260/239.3 |
| 4,425,319 | 1/1984 | Yokoyama et al. ............ 424/1.1 |
| 4,585,780 | 4/1986 | Hider et al. ............ 514/348 |
| 4,637,929 | 1/1987 | Quay ............ 436/806 X |
| 4,647,447 | 3/1987 | Gries et al. ............ 424/9 |
| 4,758,422 | 7/1988 | Quay ............ 436/806 X |

FOREIGN PATENT DOCUMENTS

8633082 7/1982 Australia .
0133603 2/1985 European Pat. Off. .

OTHER PUBLICATIONS

J. Huberty, et al., The Society of Magnetic Resonance in Medicine, 1983, pp. 175-176.
Anderegg, et al.; Helv. Chim. Acta, 46; 1400-1407; 1963.
Hoffer, et al.; Radiology, 131; 775-779; 1979.
Merck Index, 9th Ed.; p. 374; No. 2837, Deferoxamine.
Chem. Absts.; 68:16758 Ln (Yunice, et al.), Arch. Environ. Health, 16 (2); 163-170 (19-68).
Carr, et al.; Clin. Radiol. 36; 561-568; 1985.

Primary Examiner—Sam Rosen
Attorney, Agent, or Firm—Cushman, Darby & Cushman

[57] ABSTRACT

A process for making a solution of a complex of an oxamine and a polyvalent paramagnetic metal comprising contacting a solution of the oxamine with (a) the insoluble hydroxide of the polyvalent paramagnetic metal in water, or (b) an alkoxide of the metal is a nonaqueous solvent, thereby to form a solution of a complex of the oxamine and the metal. The complex, preferably ferrioxamine, is an improved NMR image enhancer compared even with ferrioxamine made conventionally, characterized by a high $LD_{50}$.

14 Claims, No Drawings

PREPARATION OF OXAMINE COMPLEXES

This is a continuation-in-part of application Ser. No. 826,827, filed Feb. 6, 1986, now U.S. Pat. No. 4,758,422, issued July 19, 1988, which is a continuation-in-part of Application Ser. No. 688,733, filed Jan. 4, 1985, now U.S. Pat. No. 4,637,929, issued Jan. 20, 1987.

U.S. Pat. No. 4,758,422 relates to an improvement in NMR imaging of a subject, such as a patient's organs, wherein there is employed as an image enhancer a complex of an oxamine and a polyvalent paramagnetic metal.

It is an object of the invention to provide an improved process for producing the image-enhancing complex of the oxamine.

It is another object of the invention to provide an improved injectable solution of an oxamine complex useful in organ imaging by magnetic resonance.

These and other objects and advantages are realized in accordance with the present invention pursuant to which there is provided a complex of an oxamine such as desferrioxamine and a polyvalent paramagnetic metal which complex when dissolved in water to a concentration of 200 g/l has an osmolarity below about 1000 mOsmol/kg. The complex, presumably because of its low osmolarity in useful concentrations, is characterized by pharmaceutically acceptable safety limits, with a high $LD_{50}$, e.g. in excess of about 300 mg/kg, advantageously in excess of 500 mg/kg and preferably in excess of about 750 mg/kg.

J. Huberty et al. (The Society of Magnetic Resonance in Medicine (1983) pp 175-176) describes making paramagnetic ion chelates of desferrioxamine in 0.35 N Hepes buffer, pH 7.3. The ferrioxamine formed has a very high osmolarity, which increases its toxicity and pain on injection, and must be used promptly after formation, since iron hydroxide precipitates rapidly in 0.35 N Hepes buffer. The reference does not describe doses which are useful for imaging.

Desferrioxamine is another term for a small group of unsubstituted trihydroxamic acids, principally the compound of the formula

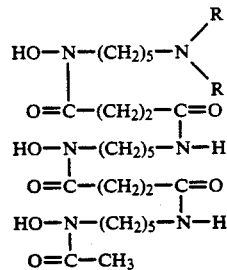

in which R is hydrogen commonly referred to as desferinrioxamine B (sold by Ciba-Geigy Corporation under the trademark Desferal). Other oxamines which can be used are those wherein each R independently is $C_{1-18}$-alkyl, $C_{3-8}$-cycloalkyl, $C_{1-18}$-alkyl-CO- or $C_{3-8}$-cycloalkyl-CO-.

The polyvalent paramagnetic metal is one which forms hydroxide or alkoxide and advantageously is manganese, copper, cobalt, a lanthanide or, preferably, iron. Such metal is provided in quantity to be fully taken up by the desferrioxamine. Thus, for example, if the paramagnetic metal is iron, the desferrioxamine is converted to ferrioxamine. Advantageously the alcohol moiety of the alkoxide is of a lower alkanol, e.g. methyl, ethyl or isopropyl.

In one embodiment, the novel complex is produced by contacting a solution of a salt of the metal, e.g. ferric chloride, with alkali, followed by washing the resulting ferric hydroxide precipitate with water to remove byproduct NaCl. Then the insoluble salt-free hydroxide is contracted with a solution of a complex of an oxamine to form a solution of the metal, e.g. a ferrioxamine solution. Advantageously the insoluble hydroxide, e.g. ferric hydroxide, is employed in excess so that after a predetermined time interval, the ferrioxamine solution is withdrawn from remaining excess insoluble hydroxide.

In another embodiment, the novel complex is produced by direct reaction of ferric(hydroxide)oxide, Fe(0)OH, with a solution of the oxamine to form a salt-free ferrioxamine solution. The ferric(hydroxide)oxide can be employed stoichiometrically or in excess and the ferrioxamine solution filtered to remove the insoluble ferric(hydroxide) oxide.

The oxamine employed in the process may be in the form of a salt such as the mesylate, chloride, or the like. The pH of the initial solution is advantageously about 3 to 8 and preferably about 4 to 6, and the pH of the resulting solution is advantageously about 4 to 8 and preferably about 4 to 6. The temperature may range from below room temperature up to the boil, but room temperature has proven adequate.

The time of contact is not critical, varying with temperature and concentration. With a concentration of about 10 to 500 and preferably about 20 to 300 grams of oxamine per liter of water and the theoretical (or excess) quantity of ferric hydroxide, for example, conversion to ferrioxamine is complete in less than an hour at room temperature, as evidenced by marked color change.

In another process, the metal may be employed as an alkoxide and the reaction effected in a non-aqueous solvent, e.g. a lower alkanol. Thus, ferric methanolate (methoxide) can be reacted with desferrioxamine in methanol to form ferrioxamine and methanol. Thereafter the ferrioxamine can be isolated as by lyophilization or precipitation from the methanol using acetone.

Thereafter the ferrioxamine, if in solution, can be dried and stored, later to be made up to an injectable solution, with optional addition of buffers, etc. Alternatively, such additives can be added before drying so the dried product need only be diluted with water to be thereafter used in conventional manner.

The invention will be further described with reference to the following illustrative example wherein all parts are by weight unless otherwise expressed.

EXAMPLE 1 Preparation of Ferrioxamine via Ferric tris(hydroxide)

Five g (18.5 mmols) of ferric chloride hexahydrate are dissolved in 100 ml of water with stirring. To this 55.5 mmols of sodium hydroxide are added dropwise, forming a precipitate of $Fe(OH)_3$. The suspension is centrifuged and washed with water four times. At this time the spent wash fluid gives a negative test for chloride (using silver nitrate). The $Fe(OH)_3$ pellet is suspended in 35 ml of water and 10.1 g of desferrioxamine B mesylate is added with stirring. The ferric hydroxide dissolves in less than one hour, giving a brick red solution of ferrioxamine. The ferrioxamine thus formed is diluted to 200 mg/ml and filter sterilized.

The osmolarity of the 200 mg/ml solution is 407 mOsmol/kg and its $LD_{50}$ is $>840$ mg/kg. The osmolarity of the 200 mg/ml solution prepared by conventional techniques is 2363-2386 mOsmol/kg and its $LD_{50}$ about 300 mg/kg.

EXAMPLE 2 Preparation of Ferrioxamine via Ferric(Hydroxide) Oxide

Twenty grams (30.5 mmols) of desferrioxamine mesylate were dissolved in 70 mL of water with stirring. To this, 2.71 g of ferric(hydroxide) oxide were added, and the suspension was stirred at 50° C. for 24 hours. By this time, the solution had acquired the brick-red color of ferrioxamine. The ferrioxamine thus formed was diluted to 200 mg/mL, as determined by spectrophotometric absorption at 430 nm. The solution was filter sterilized, and had an osmolarity of 797 mOsm/kg and a pH of 4.6.

EXAMPLE 3 Preparation of Ferrioxamine via Ferric Methoxide

Twenty grams (30.5 mmoles) of desferrioxamine mesylate and 4.54 g of iron (III) methoxide were suspended in 100 mL methanol. The mixture was heated at 50° C. with stirring for nine hours, during which time the solution developed the brick red color of ferrioxamine. The solution thus formed was filtered and evaporated to dryness. The resulting dark red solid was dissolved in 100 mL of water, yielding a 142 mg/mL solution of ferrioxamine, as determined by spectrometric absorption at 430 nm. The osmolarity of this solution was 1470 mOsm/kg, and its pH was 8.3.

It will be understood that the specification and examples are illustrative but not limitative of the present invention and that other embodiments within the spirit and scope of the invention will suggest themselves to those skilled in the art.

What is claimed is:

1. A process for preparing an oxamine-polyvalent paramagnetic metal complex comprising reacting, in a solvent at a pH of about 3 to 8, an oxamine having the formula:

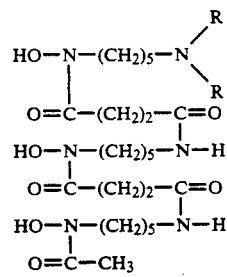

in which each R, independently, is a hydrogen atom or a $C_{1-18}$-alkyl, $C_{3-8}$-cycloalkyl, $C_{1-18}$-alkyl-CO- or $C_{3-8}$-cycloalkyl-CO-group, or a salt thereof, with the hydroxide or alkoxide of a polyvalent paramagnetic metal.

2. A process according to claim 1 in which the pH is about 4-6.

3. A process according to claim 11 using a polyvalent paramagnetic metal hydroxide and water as the solvent.

4. A process according to claim 3, wherein the polyvalent paramagnetic metal is iron, manganese, copper, cobalt or a lanthanide.

5. A process according to claim 4, wherein the polyvalent paramagnetic metal is iron.

6. A process according to claim 4 wherein the polyvalent paramagnetic metal is manganese.

7. A process according to claim 4 wherein the polyvalent paramagnetic metal is a lanthahide.

8. A process according to claim 1 wherein each R, independently, is a hydrogen atom or a $C_{12-18}$-alkyl-CO-group.

9. A process according to claim 1 wherein each R, independently, is a hydrogen atom.

10. A process according to claim 1 wherein the polyvalent paramagnetic metal is iron.

11. A process according to claim 1 wherein the polyvalent paramagnetic metal is manganese.

12. A process according to claim 1 wherein the polyvalent paramagnetic metal is a lanthahide.

13. A process according to claim 4 wherein the oxamine is trihydroxamic acid and the polyvalent paramagnetic metal is iron.

14. A process according to either of claims 4 or 13 wherein the oxamine is in the form of its mesylate salt.

* * * * *